(12) United States Patent
Fan et al.

(10) Patent No.: US 10,278,671 B2
(45) Date of Patent: May 7, 2019

(54) SHEAR WAVE DETECTION IN MEDICAL ULTRASOUND IMAGING

(71) Applicants: Liexiang Fan, Sammamish, WA (US); Seungsoo Kim, Kirkland, WA (US); Nikolas Ivancevich, Seattle, WA (US)

(72) Inventors: Liexiang Fan, Sammamish, WA (US); Seungsoo Kim, Kirkland, WA (US); Nikolas Ivancevich, Seattle, WA (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 468 days.

(21) Appl. No.: 14/042,424

(22) Filed: Sep. 30, 2013

(65) Prior Publication Data
US 2015/0094579 A1    Apr. 2, 2015

(51) Int. Cl.
| | |
|---|---|
| A61B 5/00 | (2006.01) |
| A61B 8/00 | (2006.01) |
| A61B 8/08 | (2006.01) |
| G01S 7/52 | (2006.01) |

(52) U.S. Cl.
CPC .............. *A61B 8/085* (2013.01); *A61B 8/485* (2013.01); *A61B 8/5269* (2013.01); *A61B 8/587* (2013.01); *G01S 7/52042* (2013.01); *A61B 5/7203* (2013.01); *G01S 7/52022* (2013.01)

(58) Field of Classification Search
None
See application file for complete search history.

(56) References Cited

U.S. PATENT DOCUMENTS

| | | | |
|---|---|---|---|
| 6,770,033 B1 | 8/2004 | Fink et al. | |
| 8,118,744 B2 | 2/2012 | Palmeri et al. | |
| 2007/0006651 A1* | 1/2007 | Kruger | G01N 29/11 73/579 |
| 2008/0249408 A1* | 10/2008 | Palmeri et al. | 600/438 |
| 2010/0016718 A1* | 1/2010 | Fan et al. | 600/438 |
| 2010/0286516 A1 | 11/2010 | Fan et al. | |
| 2012/0089019 A1 | 4/2012 | Fan | |
| 2012/0226158 A1* | 9/2012 | Greenleaf et al. | 600/438 |
| 2013/0131511 A1 | 5/2013 | Peterson et al. | |
| 2013/0245442 A1* | 9/2013 | Hazard | G01S 7/52036 600/438 |

OTHER PUBLICATIONS

Palmeri, et al., "Quantifying Hepatic Shear Modulus In Vivo Using Acoustic Radiation Force", Ultrasound in Medicine and Biology, New York, NY, US, vol. 34, No. 4, Jan. 25, 2008, pp. 546-558.
McLaughlin, Joyce, et al., "Shear wave speed recovery in transient elastography and supersonic imaging using propagating fronts", Inverse Problems, Institute of Physics Publishing, Bristol, GB, nol. 22, No. 2, Apr. 1, 2006, pp. 681-706.
EP Search Report dated Feb. 27, 2015 from counterpart EP application No. 14183646.0, 8 pages.

\* cited by examiner

*Primary Examiner* — Michael J Carey
*Assistant Examiner* — Don N Ho

(57) ABSTRACT

Shear waves are detected with ultrasound. The detection of the shear wave is constrained using prior measurements in a more controlled environment (e.g., less noise). For example, shear waves measured in a phantom are used to constrain the detection of shear waves in a patient to avoid false positive detections.

13 Claims, 2 Drawing Sheets

SHEAR WAVE DETECTION IN MEDICAL ULTRASOUND IMAGING

BACKGROUND

The present embodiments relate to shear wave ultrasound imaging. Shear waves traveling through tissue may be detected. The shear velocity or other characteristics of the shear wave may indicate diagnostically useful information about the tissue, such as the stiffness of the tissue. Cysts, dead tissue, or other abnormally stiff or soft tissue may be detected using shear wave ultrasound imaging.

Detecting shear waves propagating in tissue may suffer from high levels of noise due to motion of the tissue relative to the transducer probe. Since ultrasound is used, the acoustic reflections or reverberation may also contribute to noise in detecting shear waves. Detection of the shear wave using peak detection in displacement, correlation lag, or other techniques may be less reliable due to the noise.

BRIEF SUMMARY

By way of introduction, the preferred embodiments described below include methods, instructions, and systems for shear wave detection with ultrasound. The detection of the shear wave is constrained using prior measurements in a more controlled environment (e.g., an environment with less noise). For example, shear waves measured in a phantom are used to constrain the detection of shear waves in a patient to avoid false peak detections.

In a first aspect, a method is provided for shear wave detection with ultrasound. A transducer transmits an acoustic radiation force excitation into a patient. Ultrasound is used to measure displacements at a location of tissue within a patient in response to a shear wave resulting from the acoustic radiation force excitation. A processor determines a maximum displacement of the displacements. A time range is identified as a predetermined constraint, from a memory, based on the maximum displacement. The processor locates a time from the displacements within the time range and calculates a shear wave velocity as a function of the time. An indication of the shear wave velocity is displayed.

In a second aspect, a non-transitory computer readable storage medium has stored therein data representing instructions executable by a programmed processor for shear wave detection with ultrasound. The storage medium includes instructions for determining a first attribute of displacements over time for a location in a patient, the displacements responsive to a shear wave, looking-up a prior second attribute as a function of the first attribute, constraining a search range for the displacements with the prior second attribute, and detecting the shear wave using the search range.

In a third aspect, a system is provided for shear wave detection with ultrasound. A transducer is configured to transmit an acoustic impulse excitation into a patient and is configured to scan with ultrasound a region of the patient. A receive beamformer is configured to generate data representing the region at different times after the acoustic impulse excitation. The data is generated from the scan with ultrasound. A processor is configured to estimate, from the data, tissue displacements caused by a shear wave induced by the acoustic impulse excitation, to estimate a characteristic of the shear wave from the tissue displacements, and to limit a search of the estimated tissue displacements for estimating the characteristic. The search is limited using prior information acquired with a same configuration of the acoustic impulse excitation.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Shear wave detection may be improved by constraining the search range. A set of attributes (e.g., displacement magnitude and travel time) of the displacement waveform measured in a controlled environment is used to constrain detection in a patient. An example controlled environment is phantoms measured with a same shear wave inducing excitation transmit configuration. Both confidence level of the detection and the accuracy of the estimation of the tissue's mechanical property or properties may be improved even with low signal-to-noise displacement data.

Figure 1:
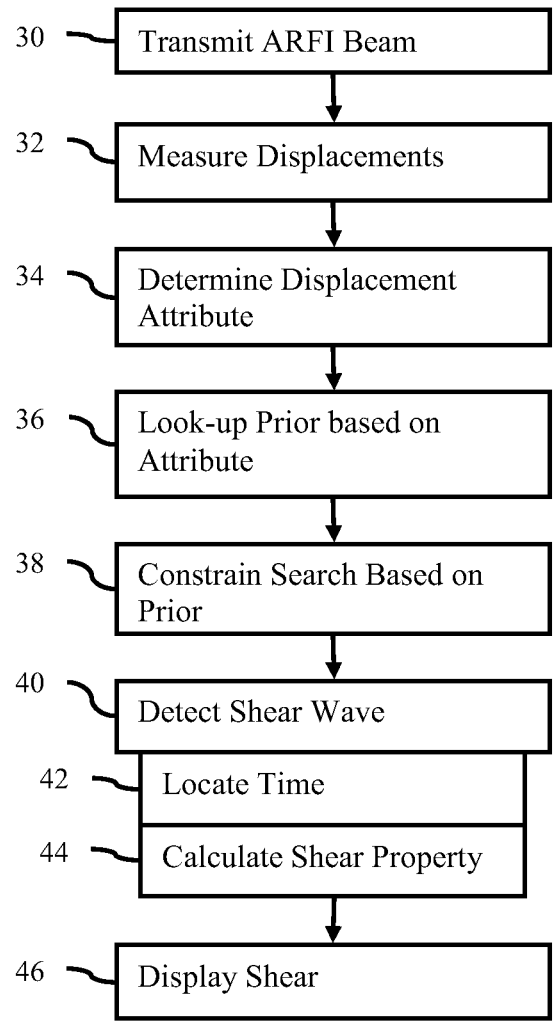
FIG. 1 is a flow chart diagram of one embodiment of a method for shear wave detection with ultrasound.

FIG. 1 shows a method for shear wave detection with ultrasound. The method is implemented by the system of FIG. 3 or a different system. Additional, different, or fewer acts may be provided. For example, act 42 is representative, and techniques other than time detection may be used to detect the shear wave. As another example, the displaying of act 46 is optional. The acts are performed in the order described or shown, but may be performed in other orders.

In act 30, an acoustic excitation is transmitted into a patient. The acoustic excitation acts as an impulse excitation for causing displacement. For example, a 400 cycle transmit waveform with power or peak amplitude levels similar or lower than B-mode transmissions for imaging tissue is transmitted as an acoustic beam. In one embodiment, the transmission is a shear wave generating sequence applied to the field of view. Any acoustic radiation force impulse (ARFI) or shear wave imaging sequence may be used.

The transmission is configured by power, amplitude, timing, or other characteristic to cause stress on tissue sufficient to displace the tissue at one or more locations. For example, a transmit focus of the beam is positioned near a bottom, center of the field of view or region of interest (ROI) to cause displacement throughout the field of view. The transmission may be repeated for different sub-regions or ROIs. Any transmit configuration, including aperture, frequency, focal location, amplitude, F#, or other characteristic may be used.

The excitation is transmitted from an ultrasound transducer. The excitation is acoustic energy. The acoustic energy is focused, resulting in a three-dimensional beam profile. The excitation is focused using a phased array and/or mechanical focus. The excitation may be unfocused in one dimension, such as the elevation dimension. The excitation is transmitted into tissue of a patient.

The impulse excitation generates a shear wave at a spatial location. Where the excitation is sufficiently strong, a shear wave is generated. The shear wave propagates through tissue more slowly than the longitudinal wave propagates along the acoustic wave emission direction. This difference in timing is used to isolate the shear wave from a longitudinal wave, such as sampling at locations at certain times. A time range covering likely passing (e.g., from arrival through exit of the shear wave) is sampled for displacements.

The shear wave propagates various directions, including a direction perpendicular to the direction of the applied stress. The displacement of the shear waves is greater at locations closer to the location at which the shear wave is generated. As the shear wave travels, the magnitude of the shear wave attenuates.

In act 32, a displacement response to the shear wave in the patient is detected. The tissue is forced to move in the patient. For example, the displacement profiles for two locations are demonstrated in FIG. 2. The excitation causes displacement of the tissue. A shear wave is generated and propagates from the focal region. As the shear wave travels through tissue, the tissue is displaced. Timing and/or lateral location are used to distinguish the shear wave from other generated waves. Longitudinal waves or other causes of displacement may be used instead of shear.

Figure 2:
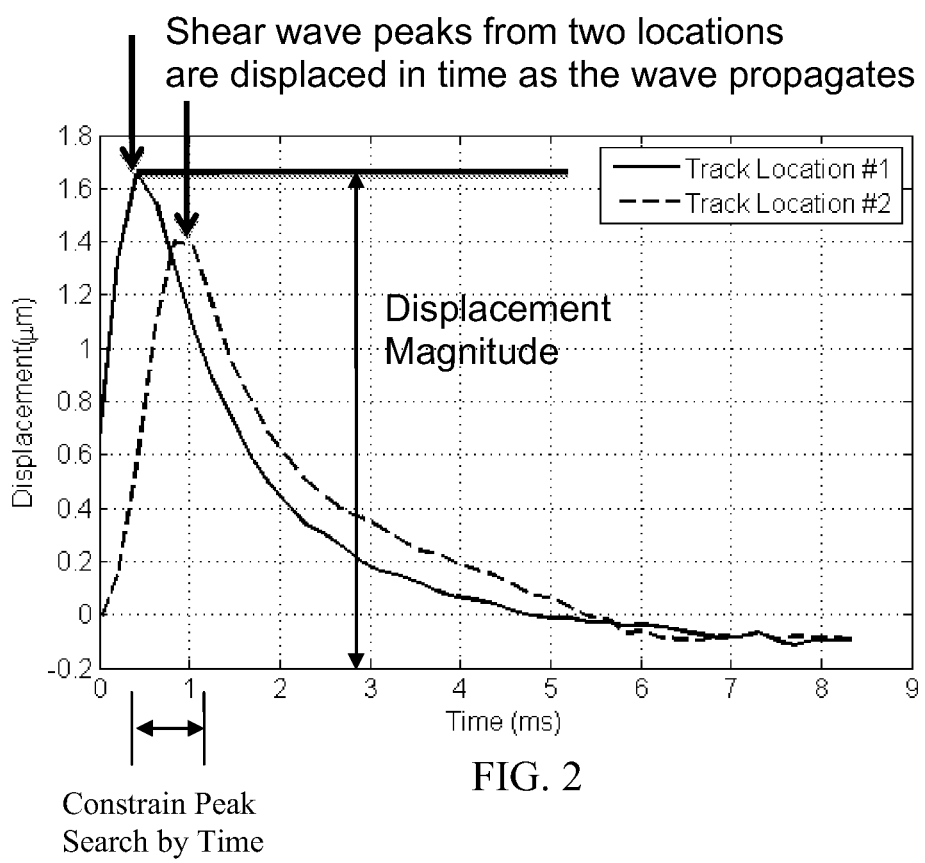
FIG. 2 is a graph showing two example displacement profiles of displacement as a function of time.

The displacement caused by the force or stress is measured. The displacement is measured over time at one or more locations. The times used to measure are set to capture the shear wave rather than a longitudinal wave. The displacement measurement may begin before the stress or impulse ends, such as using a different frequency or coding. Alternatively, the displacement measurement begins after the impulse ends. Since the shear, longitudinal or other wave causing the displacement in tissue spaced from the point or region of stress takes time to travel, the displacement from a relaxed or partially stressed state to a maximum displacement and then to a relaxed state may be measured, as represented in FIG. 2. A temporal profile of displacement is determined. Alternatively, the displacement is measured only while the tissue is relaxing from just before, at or near the likely maximum.

The measurement is of the amount or magnitude of the displacement. The tissue is moved in any direction. The measurement may be along the direction of greatest movement. The magnitude of the motion vector is determined. Alternatively, the measurement is along a given direction, such as perpendicular to the scan line regardless of whether the tissue is displaced more or less in other directions.

The displacement is detected with ultrasound scanning. Ultrasound data is obtained. At least some of the ultrasound data is responsive to the shear wave. A region, such as a region of interest, entire field of view, or sub-region of interest, is scanned with ultrasound. The region is monitored to detect the shear wave. The region is any size, such as 5 mm in lateral and 10 mm in axial. For example, B-mode scans are performed to detect tissue displacement caused by the shear wave. Doppler, color flow, or other ultrasound mode may be used to monitor for the shear wave.

For a given time, ultrasound is transmitted to the tissue or region of interest. Any now known or later developed displacement imaging may be used. For example, pulses with 1-5 cycle durations are used with an intensity of less than 720 mW/cm$^2$. Pulses with other intensities may be used. The monitoring is performed for any number of scan lines. For example, four or eight receive beams are formed in response to each transmission. After transmitting the excitation to generate the shear wave, B-mode transmissions are performed repetitively along a single transmit scan line and receptions along four or eight adjacent receive scan lines. In other embodiments, only a single receive beam or other numbers of receive beams are formed in response to each transmission. Additional transmit scan lines and corresponding receive line or lines may be used. Any number of repetitions may be used, such as about 120 times. Some of the ultrasound data, such as at the beginning or end of the repetitions, may not be responsive to the shear wave. Any range of times for measuring displacements for a given location may be used.

As the shear wave propagates through the scan lines, the B-mode intensity may vary due to displacement of the tissue. For the monitored scan lines, a sequence of data is provided representing a time profile of tissue motion resulting from the shear wave. Echoes or reflections from the transmission are received. The echoes are beamformed, and the beamformed data represents one or more locations. To detect the displacement, ultrasound energy is transmitted to the tissue undergoing displacement and reflections of the energy are received. Any transmission and reception sequence may be used.

By performing the transmitting and receiving multiple times, data representing a one, two, or three-dimensional region at different times is received. The transmission and reception are performed multiple times to determine change due to displacement. By repetitively scanning with ultrasound, the position of tissue at different times is determined.

The displacement is detected from the differences for each spatial location. For example, the velocity, variance, shift in intensity pattern (e.g., speckle tracking), or other information is detected from the received data as the displacement.

In one embodiment using B-mode data, the data from different scans is correlated as a function of time. For each depth or spatial location, a correlation over a plurality of depths or spatial locations (e.g., kernel of 64 depths with the center depth being the point for which the profile is calculated) is performed. For example, a current set of data is correlated multiple times with a reference set of data. The location of a sub-set of data centered at a given location in the reference set is identified in the current set. Different relative translations and/or rotations between the two data sets are performed.

The reference is a first set of data or data from another scan. The reference set is from before the ARFI pulse, but may be from after the ARFI pulse. The same reference is used for the entire displacement detection, or the reference data changes in an ongoing or moving window.

The correlation is one, two or three-dimensional. For example, correlation along a scan line away and toward the transducer or along a line perpendicular to the scan line is used. As another example, the translation is along two axes with or without rotation. In yet another example, the translation is along three axes with or without rotation about three or fewer axes. The level of similarity or correlation of the data at each of the different offset positions is calculated. The translation and/or rotation with a greatest correlation represents the motion vector or offset for the time associated with the current data being compared to the reference.

Any now known or later developed correlation may be used, such as cross-correlation, pattern matching, or minimum sum of absolute differences. Tissue structure and/or speckle are correlated. Using Doppler detection, a clutter filter passes information associated with moving tissue. The velocity of the tissue is derived from multiple echoes. The velocity is used to determine the displacement towards or away from the transducer. Alternatively, the relative or difference between velocities at different locations may indicate strain or displacement.

FIG. 2 shows two example displacement profiles. The magnitude in distance of the motion vector over time from the reference data is shown. The period of analysis is over about 8 milliseconds, but may be longer or shorter (e.g., 12 milliseconds at a 4.8 kHz sample rate). Other displacement profiles are possible, such as a profile with multiple peaks due to noise. Any number of locations may be measured for displacement, such as measuring every millimeter in the 10×5 mm region of interest. Displacement for each location and for each sample time is measured.

In act 34, an attribute of the displacements from the patient is determined. The displacements at different times for a given location are used. For example, the displacement profile, a curve fit to the displacements over time, or the displacements over time without specifically determining the curve or profile are used.

A processor determines the attribute. Any attribute may be used. The attribute relates to the timing, magnitude, or both. For example, an integral of displacement over time, a slope of the displacement increase or decrease, or other attribute is determined. In one embodiment, the maximum magnitude is determined. The maximum displacement is calculated from the displacement profile. The peak or highest amount of motion or magnitude of shift of the tissue along a line, within a plane, or within a volume is calculated for the peak. The smoothed or filtered displacement curve may be used for the maximum calculation. In other embodiments, the raw or unfiltered displacement curve may be used. Alternatively, the magnitude may be from a given time based on a distance from the focal region to the monitored location.

FIG. 2 shows a maximum displacement magnitude of about 1.40 micrometers for one displacement profile and about 1.65 micrometers for another. This amplitude of the displacement shows the maximum shift in position caused by the shear wave plus any offset (inaccuracy) caused by other undesired sources (e.g., noise sources).

The maximum displacement over time for each location is found. The maximum value over the entire or portion of the profile is identified or determined. The maximum is within the time range over which displacement is measured, such as being over 8-12 milliseconds (e.g., FIG. 2 shows about 8 milliseconds). Alternatively, the maximum is sought over a portion of the sampling time, such as over a first half (e.g., 4 milliseconds in the FIG. 2 example).

The temporal profile for a given location indicates detection of the shear wave at that location. The profile is examined for a non-noise or single instance of variation. A peak in the profile, with or without temporal low pass filtering, indicates the passing of the shear wave front. The greatest displacement is selected, but the average, initial non-noise displacement, or other displacement statistic may be used to indicate the passing. Since noise may be a concern, the timing of the peak or maximum displacement may not be as accurate as desired. Similarly, the magnitude may not be as accurate as desired.

In act 36, another attribute is looked-up from a memory using the attribute from the displacements measured in the patient. For example, a time or time range is looked-up based on the maximum displacement. Other attributes than time may be looked-up, such as a maximum displacement (e.g., look-up a prior maximum displacement from the measured maximum) or detection configuration.

The other attribute represents prior knowledge. A phantom or other more controlled environment measurements are made to populate a table. Controlled environments may include mechanical systems to hold the patient or the transducer, patients with more ideal imaging anatomy (e.g., less fat layers), patients holding their breath, phantoms, or combinations thereof. Phantoms and mechanically supported scanning environments provide more control over the measurements.

Tissue or phantoms mimicking tissue of different stiffnesses or other properties are measured. For example, a plurality of different phantoms representing a range of likely or possible tissue stiffnesses are measured. The resulting time or a time range based on the resulting time is recorded along with the maximum displacement. The maximum displacement is used as an index to select the time or time range. A table associating any attribute to another attribute in the more controlled environment may be used.

A table is provided for each possible transmit configuration. Since the characteristics of the ARFI may vary, the resulting maximum displacement and times may be different for different transmit configurations. Alternatively, the transmit configuration for measuring from the patient is limited to configurations similar to or the same as configurations used to establish the tables. Due to attenuation, different tables may be provided for different locations. A set of tables is provided for each location. The tables for the different locations may have the same or different attribute values. Alternatively, one or more locations share the same tables.

In the embodiment relating maximum displacement to time, the time is of the maximum displacement occurring in the controlled environment (e.g., phantom measurements). The time is output and used to establish a time range. Any tolerance may be used. The tolerance is symmetrical or asymmetrical. Different or equal amounts of time may be added and subtracted from the time to establish the time range. Alternatively, the time range is stored in the table and output.

The time range has a period less than the time over which displacement is sampled and/or over which the maximum displacement was searched in the measurements from the patient. In the example of FIG. 2, displacements are sampled over 8 milliseconds. The time range output from or derived from the time output from the table is less, such as being an order of magnitude less. In one embodiment, the time range is 0.5 milliseconds in duration. Greater or lesser ranges may be used.

The time range represents an expected time or possible times given the maximum displacement detected in the patient. The maximum displacement is an indication of the tissue stiffness. This indication is used to find the expected time or times for the peak or passing of the shear wave from the prior knowledge.

In act 38, the expected attribute from the prior information (e.g., from phantom measurements) is used to constrain the detection of the shear wave in act 40. For example, an aspect of detection is limited to be at, below, above, or near a value or within a range. As another example, the technique used, process flow, steps taken, or variable value used in detection is set based on the expected attribute. The detection is configured differently for different expected attributes. Rather than outputting the expected attribute itself, the table may include the configuration information.

In one embodiment, a search range is limited. For example, the maximum displacement or a peak displacement over time is to be found. The amplitude of the maximum over a longer range of time is used to look-up the expected time or shorter time range for detecting passing of the shear wave. The expected time or time range is used to limit the search for the peak to calculate shear wave velocity. The peak or maximum found in the expected time range may be different than (e.g., less than) or the same peak found to look-up the expected time. Due to noise, multiple peaks may occur for the displacement profile. The time of the occurrence of the peak in maximum displacement within the limited time range is used for the shear wave velocity calculation. By limiting the range, any noise-caused peaks outside the expected range are not used for detection of the shear wave.

In act 40, the shear wave is detected. The detecting is constrained based on the prior information. Due to configuration, search range limiting, a threshold value, or other setting preventing a broader detection, the detection of the shear wave at a location is constrained. For example, the search range for the maximum displacement to identify a time of passing, initiation, maximum, completion, or other aspect of the shear wave at the location is calculated.

A processor performs the calculation. The displacement information is used to determine the property without user input. Once the displacements are acquired, the processor automatically calculates the property for each location and/or time as constrained by the prior information.

The shear wave property is detected from the displacements. The displacements over time and/or space are used. In one embodiment, the displacements for different depths are combined, leaving displacements spaced in azimuth or along the propagation direction of the shear wave. For example, the displacements for a given scan line or lateral location are averaged over depth. Alternatively to averaging, a maximum or other selection criterion is used to determine the displacement for a given lateral location.

For detecting the shear wave velocity, amplitude peak detection or correlation lag detection may be used. The time of passing of the shear wave is located in act 42 from the displacement profile. For peak detection with the prior information limiting the search range, the time of the peak or maximum displacement (e.g., maximum peak) within the search range of times is located. The time of occurrence of the peak displacement is located. The time is an absolute time or a measure relative to creation of the shear wave. For correlation lag detection with the prior limiting the search range, a sliding window is used to correlate displacement profiles. The window slides in time and is limited to within the search range established with the prior knowledge. The correlation is between different displacement profiles (i.e., between different locations). The correlation lag associated with the highest correlation of profiles indicates a delay or travel time between locations. The search range limits the times for which this highest correlation between profiles is sought. The delay or travel time from the highest correlation within the search range may be extrapolated, accumulated, or otherwise used to find the time from generation of the shear wave to passing at a given location.

Other techniques may be used to detect the peak in the profile and corresponding time and velocity. For example, a regression is applied. Since the shear wave peak displacement time is a linear function of distance, a robust linear regression with automated outlier detection may indicate the shear wave velocity, or slope. The ultrasound data for all of the sample points in the region of interest is plotted for distance as a function of time or by time and distance. The linear regression is applied to the plot or data, providing a line fit to the data. The slope of the line indicates the shear wave velocity. The displacements used in the regression are time limited and/or the fit is limited to a range of slopes.

Once the shear wave is detected (e.g., time determined), the velocity or other characteristic of the shear wave is determined in act 44. For example, the processor calculates the shear wave velocity from the time of occurrence of the shear wave at the location and the distance from the origin of the shear wave to the location. The travel time is the inverse of the velocity. Using the distance and the travel time, the velocity is calculated. The distance is known from the scan line spacing (i.e., the transmit beam position for generating the shear wave and the receive beam position for detecting the shear wave).

One or more shear wave characteristics are calculated. Shear wave characteristics include various possible parameters or properties, such as attenuation, center frequency, or bandwidth. Any characteristic of the shear wave may be used to detect the shear wave at the location. Tissue characteristics derived from the shear wave characteristic may be calculated, such as the Young's or other modulus.

The measuring of act 32, determining of act 34, identifying of act 36, constraining of act 38, detecting of act 40, locating of act 42, and calculating of act 44 are repeated for other locations. The same shear wave passing through other locations is detected. The transmission of act 30 and subsequent acts may be repeated for the same or other locations. Where the shear wave detection involves displacements from multiple locations, acts 32 and/or 34 are repeated. Different combinations of acts may be repeated for generating a single image. Other repetition may be repeated to generate a sequence of images. Alternatively, no repetition is provided.

In act 46, an indication of the shear wave velocity, other shear wave characteristic, or tissue characteristic derived from the shear wave characteristic is displayed. The shear wave velocity, modulus or other information determined from tissue reaction to a shear wave is displayed. Shear velocity is used as an example below. A value or image that is a function of the shear wave characteristic is displayed. For example, an image of shear wave velocity by location in one, two, or three-dimensional representation is displayed. The shear velocity as a function of location is displayed by color, brightness, hue, luminance, or other modulation of display values in a two-dimensional representation. Any shear imaging may be used. The displayed image represents shear wave information for the region of interest or the entire imaging region. For example, where shear velocity values are determined for all of the grid points in a region of interest or field of view, the pixels of the display represent the shear wave velocities for that region. The display grid may be different from the scan grid and/or grid for which displacements are calculated.

The shear wave information is used for a color overlay or other modulation of display values. The shear data is in a display format or may be scan converted into a display format. The shear data is color or gray scale data, but may be data prior to mapping with gray scale or color scale. The information may be mapped linearly or non-linearly to the display values.

The image may include other data. For example, shear wave information is displayed over or with B-mode information. B-mode or other data representing tissue, fluid, or contrast agents in the same region may be included, such as displaying B-mode data for any locations with shear wave velocity below a threshold or with poor quality. The other data assists the user in determining the location of the shear information. In other embodiments, the shear wave characteristic is displayed as an image without other data.

In one embodiment, a value representing the shear wave velocity is displayed on a screen. Alternatively or additionally, a graphic (e.g., curve or icon) representing the shear velocity is displayed. Reference to a scale or other reference may be displayed. The shear velocity is indicated alone or with other shear wave information. For example, shear wave imaging is performed as well as displaying a textual (e.g., alphanumeric) value for a location.

Figure 3:
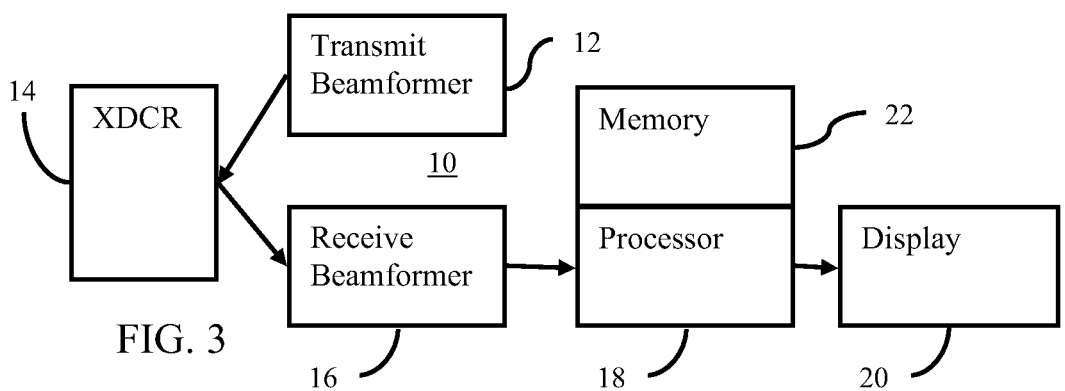
FIG. 3 is a block diagram of one embodiment of a system for shear wave detection with ultrasound.

FIG. 3 shows one embodiment of a system 10 for shear wave detection with ultrasound. The system 10 implements the method of FIG. 1 or other methods. The system 10 includes a transmit beamformer 12, a transducer 14, a receive beamformer 16, an image processor 18, a display 20, and a memory 22. Additional, different or fewer components may be provided. For example, a user input is provided for user interaction with the system.

The system 10 is a medical diagnostic ultrasound imaging system. In alternative embodiments, the system 10 is a personal computer, workstation, PACS station, or other arrangement at a same location or distributed over a network for real-time or post acquisition imaging.

The transmit beamformer 12 is an ultrasound transmitter, memory, pulser, analog circuit, digital circuit, or combinations thereof. The transmit beamformer 12 is operable to generate waveforms for a plurality of channels with different or relative amplitudes, delays, and/or phasing. Upon transmission of acoustic waves from the transducer 14 in response to the generated electrical waveforms, one or more beams are formed. A sequence of transmit beams are generated to scan a two or three-dimensional region. Sector, Vector®, linear, or other scan formats may be used. The same region is scanned multiple times. For flow or Doppler imaging and for shear imaging, a sequence of scans along the same line or lines is used. In Doppler imaging, the sequence may include multiple beams along a same scan line before scanning an adjacent scan line. For shear imaging, scan or frame interleaving may be used (i.e., scan the entire region before scanning again). Line or group of line interleaving may be used. In alternative embodiments, the transmit beamformer 12 generates a plane wave or diverging wave for more rapid scanning.

The same transmit beamformer 12 generates impulse excitations or electrical waveforms for generating acoustic energy to cause displacement. Electrical waveforms for acoustic radiation force impulses are generated. In alternative embodiments, a different transmit beamformer is provided for generating the impulse excitation. The transmit beamformer 12 causes the transducer 14 to generate pushing pulses or acoustic radiation force pulses.

The transducer 14 is an array for generating acoustic energy from electrical waveforms. For an array, relative delays focus the acoustic energy. A given transmit event corresponds to transmission of acoustic energy by different elements at a substantially same time given the delays. The transmit event provides a pulse of ultrasound energy for displacing the tissue. The pulse is an impulse excitation or tracking pulse. Impulse excitation includes waveforms with many cycles (e.g., 500 cycles) but that occurs in a relatively short time to cause tissue displacement over a longer time. A tracking pulse may be B-mode transmission, such as using 1-5 cycles. The tracking pulses are used to scan a region of a patient.

The transducer 14 is a 1-, 1.25-, 1.5-, 1.75- or 2-dimensional array of piezoelectric or capacitive membrane elements. The transducer 14 includes a plurality of elements for transducing between acoustic and electrical energies. Receive signals are generated in response to ultrasound energy (echoes) impinging on the elements of the transducer 14. The elements connect with channels of the transmit and receive beamformers 12, 16. Alternatively, a single element with a mechanical focus is used.

The receive beamformer 16 includes a plurality of channels with amplifiers, delays, and/or phase rotators, and one or more summers. Each channel connects with one or more transducer elements. The receive beamformer 16 is configured by hardware or software to apply relative delays, phases, and/or apodization to form one or more receive beams in response to each imaging or tracking transmission. Receive operation may not occur for echoes from the impulse excitation used to displace tissue. The receive beamformer 16 outputs data representing spatial locations using the receive signals. Relative delays and/or phasing and summation of signals from different elements provide beamformation. In alternative embodiments, the receive beamformer 16 is a processor for generating samples using Fourier or other transforms.

The receive beamformer 16 may include a filter, such as a filter for isolating information at a second harmonic or other frequency band relative to the transmit frequency band. Such information may more likely include desired tissue, contrast agent, and/or flow information. In another embodiment, the receive beamformer 16 includes a memory or buffer and a filter or adder. Two or more receive beams are combined to isolate information at a desired frequency band, such as a second harmonic, cubic fundamental or other band.

In coordination with the transmit beamformer 12, the receive beamformer 16 generates data representing the region at different times. After the acoustic impulse excitation, the receive beamformer 16 generates beams representing locations along a plurality of lines at different times. By scanning the region of interest with ultrasound, data (e.g., beamformed samples) is generated. By repeating the scanning, ultrasound data representing the region at different times after the impulse excitation is acquired.

The receive beamformer 16 outputs beam summed data representing spatial locations. Data for a single location, locations along a line, locations for an area, or locations for a volume are output. The data may be for different purposes. For example, different scans are performed for B-mode or tissue data than for displacement. Alternatively, the B-mode data is also used to determine displacement. As another example, data for shear imaging is acquired with a series of shared scans, and B-mode or Doppler scanning is performed separately or using some of the same data.

The processor 18 is a B-mode detector, Doppler detector, pulsed wave Doppler detector, correlation processor, Fourier transform processor, application specific integrated circuit, general processor, control processor, image processor, field programmable gate array, digital signal processor, analog circuit, digital circuit, combinations thereof or other now known or later developed device for detecting and processing information for display from beamformed ultrasound samples. In one embodiment, the processor 18 includes one or more detectors and a separate processor. The separate processor is a control processor, general processor, digital signal processor, application specific integrated circuit, field programmable gate array, network, server, group of processors, data path, combinations thereof or other now known or later developed device for determining displacement, identifying magnitude of displacement, calculating travel time, calculating shear wave velocity, calculating one or more other properties of shear wave propagation, and/or estimating fat fraction. For example, the separate processor is configured by hardware and/or software to perform any combination of one or more of the acts shown in FIG. 1.

The processor 18 is configured to estimate tissue displacement induced by the acoustic impulse excitation. Using correlation, tracking, motion detection, or other displacement measuring, the amount of shift in position of the tissue is estimated. The estimation is performed multiple times through a period, such as from prior to the tissue moving due to the impulse to after the tissue has mostly or completely returned to a relaxed state (e.g., recovered from the stress caused by the impulse excitation). The estimation is performed for each of one or more locations.

The processor 18 is configured to calculate a shear wave characteristic, such as the shear wave velocity, from the tissue displacements. For velocity, the maximum or other displacement is used to determine a travel time of the shear wave. Correlation lag using displacements from multiple locations may be used to find the travel time. The velocity is calculated using distance and the travel time. Velocity is determined for any number of locations. Linear regression may be used to find velocity for multiple locations from the displacements for those locations.

In calculating the shear velocity or other characteristic from the displacements, the processor 18 is configured to limit the calculation. For example, a search of the estimated tissue displacements for estimating the characteristic is limited to a time range. The search is limited using prior information. Information from one or more ideal or controlled scanning situations (e.g., scanning phantoms with different stiffnesses) is used for later patient imaging. This prior information is acquired with a same configuration of the acoustic impulse excitation as used for imaging the patient or other less controlled scanning. For example, a table is created. The table associates or links two or more attributes with each other, such as time linked with maximum displacement. A measure of one may be used to find the expected value of the other. Settings, such as search range limits, are established based on the expected value. When detection is performed, erroneous or noise related information may be removed or not considered due to the detection constraint.

The processor 18 is configured to generate one or more images. For example, a shear wave velocity image is generated. The shear wave velocity image is presented as an overlay or region of interest within a B-mode image. The shear wave velocity modulates the color at locations in the region of interest. Where the shear wave velocity is below a threshold, B-mode information may be displayed without modulation by the shear wave velocity.

Other information may be included in the image or displayed sequentially or substantially simultaneously. For example, a value for shear velocity, modulus, or other information for a location is displayed at a same time as the shear wave velocity image. The processor 18 may be configured to generate other displays. For example, a graph, text, or graphical indicators of the shear velocity is displayed.

The processor 18 operates pursuant to instructions stored in the memory 22 or another memory for shear wave detection with ultrasound. The memory 22 is a non-transitory computer readable storage media. The instructions for implementing the processes, methods and/or techniques discussed herein are provided on the computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing, and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

The display 20 is a CRT, LCD, projector, plasma, or other display for displaying two-dimensional images or three-dimensional representations. The two dimensional images represent spatial distribution in an area. The three-dimensional representations are rendered from data representing spatial distribution in a volume. The display 20 is configured by the processor 18 or other device by input of the signals to be displayed as an image. The display 20 displays an image representing shear for different locations in a region of interest or an entire image. The display 20 displays one or more characteristics of the shear wave.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for shear wave detection with ultrasound, the method comprising:
    transmitting, from a transducer, an acoustic radiation force excitation into a patient;
    measuring, with ultrasound, displacements at a location of tissue within a patient in response to a shear wave resulting from the acoustic radiation force excitation, the displacements measured over a first plurality of times;
    determining, by a processor, a maximum displacement in magnitude of the displacements for the location; then identifying a time range as a predetermined constraint, from a memory, based on the maximum displacement, the time range extending over a second plurality of times that is a sub-set of the first plurality of times for which the displacements are measured, and the time range being identified by the processor;
    locating, by the processor, a time from the measured displacements of the second plurality of times, the located time corresponding to a first displacement in magnitude, the first displacement at the located time being less than the maximum displacement, wherein the locating further comprises a search for the located time constrained to be within the time range such that the displacements in the sub-set of the first plurality of times are searched and not the displacements outside the sub-set of the first plurality of times, the first displacement being in the sub-set;
    calculating, by the processor, a shear wave velocity as a function of the time; and
    displaying an indication of the shear wave velocity.

2. The method of claim 1 wherein measuring the displacements comprises repetitively scanning the location with the ultrasound.

3. The method of claim 1 wherein identifying comprises identifying based on the maximum displacement in magnitude.

4. The method of claim 1 wherein determining the maximum displacement comprises determining over a displacement range of time longer than the time range, the displacement range of time comprising the first plurality of times.

5. The method of claim 1 wherein identifying the time range comprises looking-up from a table of phantom measurements under a same transmit configuration of the acoustic radiation force excitation.

6. The method of claim 1 wherein identifying the time range comprises identifying an expected time given the maximum displacement and assigning a tolerance to the expected time.

7. The method of claim 1 wherein locating the time comprises locating the first displacement as a peak displacement of the displacements within the time range and locating the time as a time of occurrence of the peak displacement.

8. The method of claim 1 wherein locating the time comprises calculating a correlation lag within the time range.

9. The method of claim 1 wherein calculating the shear wave velocity comprises calculating the shear wave velocity as a function of a distance from an origin of the shear wave to the location and the time or calculating the shear wave velocity as a function of a distance from the location to another location and the time.

10. The method of claim 1 wherein displaying the indication comprises displaying a value that is a function of the shear wave velocity.

11. The method of claim 1 wherein displaying the indication comprises displaying an image representing the shear wave velocity at the location.

12. The method of claim 1 further comprising repeating measuring, determining, identifying, locating, and calculating for other locations.

13. The method of claim 1 wherein determining and identifying links the maximum displacement and time range and at least one other attribute.

* * * * *